United States Patent [19]

Plotkin et al.

[11] Patent Number: 5,342,860

[45] Date of Patent: Aug. 30, 1994

[54] RADIATION CURABLE ALK-1-ENYL ETHER POLYESTER PREPOLYMERS

[75] Inventors: Jeffrey S. Plotkin, Monsey, N.Y.; Mark M. Miller, Ridgewood, N.J.

[73] Assignee: ISP Investments Inc., Wilmington, Del.

[21] Appl. No.: 107,867

[22] Filed: Aug. 18, 1993

[51] Int. Cl.$^5$ .................... C08F 2/50; C08F 16/32; C07C 69/347; C07C 69/767
[52] U.S. Cl. .................... 522/31; 428/421; 428/458; 428/462; 522/104; 522/107; 522/181; 526/292.3; 526/309; 526/320; 525/445; 560/95; 560/193; 560/201
[58] Field of Search .............. 522/108, 181, 31; 560/95, 193, 201; 526/292.3, 309, 320

[56] References Cited

U.S. PATENT DOCUMENTS

| | | | |
|---|---|---|---|
| 3,485,733 | 12/1969 | D'Alelio | 522/108 |
| 4,091,141 | 5/1978 | Harris | 522/108 |
| 4,749,807 | 6/1988 | Lapin | 522/108 |
| 4,845,265 | 7/1989 | Lapin | 560/193 |

*Primary Examiner*—Marion E. McCamish
*Assistant Examiner*—Arthur H. Koeckert
*Attorney, Agent, or Firm*—Marilyn J. Maue; Joshua J. Ward

[57] ABSTRACT

This invention relates to alk-1-enyl ether-polyester block prepolymers which are curable by cationically initiated radiation and which are defined by the formula $$(R_6CH=CHR_4O)_{\overline{2}}[(COACO-OR_1CHO)_mCOACO]- \\ | \\ R_2OCH=CHR_5$$

wherein
m has a value of from 1 to 25;
A is $C_2$ to $C_{12}$ alkylene, $C_6$ to $C_{14}$ aryl, both groups optionally substituted with lower alkyl, halo lower alkyl, alkyleneoxy, halogen or aryl;
$R_1$ is alkylene containing from 1 to 6 carbon atoms;
$R_2$ is a saturated or unsaturated divalent radical containing from 1 to 14 carbon atoms and is selected from the group of alkylene, alkenylene and arylene, each group optionally substituted with oxygen, halogen, lower alkyl and/or hydroxy;
$R_3$ is hydrogen or $C_1$ to $C_6$ alkyl;
$R_4$ is $C_1$ to $C_6$ alkylene, $C_6$ to $C_{14}$ arylene, lower alkyl substituted phenylene or xylylene and
$R_5$ and $R_6$ are independently hydrogen or $C_1$ to $C_4$ alkyl.
The invention also relates to the method of preparing and curing the above prepolymer and to the use of the cured prepolymer as a hard, flexible protective coating possessing high density and superior resistance to abrasion and chemical attack.

19 Claims, No Drawings

RADIATION CURABLE ALK-1-ENYL ETHER POLYESTER PREPOLYMERS

In one aspect, the present invention relates to novel prepolymers containing polyurethanyl groups and a plurality of alk-1-enyl ether crosslinking sites. In another aspect the invention relates to the preparation of said prepolymers and in still another aspect the invention relates to cured coatings of said prepolymers.

BACKGROUND OF THE INVENTION

It is known that certain polyester coating materials can be cured thermally or by radiation in the presence of a free radical photoinitiator but these materials do not lend themselves to cationically induced polymerization. It is well recognized that thermal curing is not cost efficient and that radiation curing in free radical systems is oxygen inhibited, thus requiring an inert atmosphere or the minimizing affect of a hydrogen donating component. The later expedient is not completely satisfactory since such hydrogen donating components significantly reduce the rate of reaction. Also, it has been found that polymerization or curing in free radical systems ceases almost immediately upon removing the source of radiation; thus, the cured product often contains significant amounts of unpolymerized components. Accordingly, it is an aim of research to develop monomers or oligomers which provide stable polymerizable formulations with polyester containing materials while incorporating other beneficial properties in the finished cured product. Additionally, it is desirable that such monomers or their oligomers be amenable to radiation curing at a rapid rate under mild temperature conditions by cationically induced polymerization which is not oxygen inhibited and which permits continued polymerization after removal from the source of radiation exposure.

Accordingly, it is an object of the present invention to overcome the disadvantages of previous polyester prepolymers and to provide a novel polyester prepolymer which is cationically curable at room temperature by radiation.

Another object is to provide a polyester prepolymer containing many crosslinking sites which is rapidly cured to a high density material under mild conditions.

Another object of this invention is to provide a convenient process for the preparation of the present prepolymer.

Still another object of this invention is to provide a protective coating with a cured high density prepolymer having improved hardness, flexibility, resistance to abrasion and chemical attack.

These and other objects will become apparent from the following description and disclosure.

THE INVENTION

In accordance with this invention, a polyhydroxylated alk-1-enyl ether having the formula

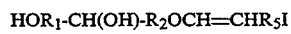

is reacted with a difunctional ester having the structure

to form an intermediate monomer or oligomer defined by the formula

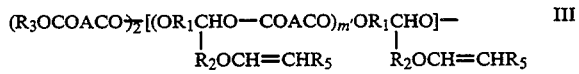

and the corresponding alcohol by-product $HOR_3$
wherein
$m'$ has a value of from 1 to 25;
A is $C_2$ to $C_{12}$ alkylene, $C_6$ to $C_{14}$ aryl, both groups optionally substituted with lower alkyl, halo lower alkyl, alkyleneoxy, halogen or aryl;
$R_1$ is alkylene containing from 1 to 6 carbon atoms;
$R_2$ is a saturated or unsaturated divalent radical containing from 1 to 14 carbon atoms and is selected from the group of alkylene, alkenylene and arylene, each group optionally substituted with oxygen, halogen, lower alkyl and/or hydroxy and
$R_3$ is hydrogen or $C_1$ to $C_6$ alkyl.

The polyhydroxylated alk-1-enyl ether reactant (I) may contain an additional OH group in the $R_2$ group which would result in an intermediate monomer or oligomer of more complex structure, i.e. where $R_3OOC-A-COOR_3$ reacts with the additional —OH group to provide another

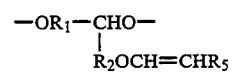

group in the side chain of the intermediate compound. However, the preferred hydroxylated alk-1-enyl ether compounds of this invention are dihydroxylated and most preferred are those wherein $R_1$ and $R_2$ are lower alkyl and $R_3$ is hydrogen, methyl or ethyl. Suitable hydroxylated alk-1-enyl ether reactants include:
1,2-dihydroxyethyl ethyl prop-1-enyl ether,
1,2-dihydroxypropyl butyl prop-1-enyl ether,
1,2-dihydroxypropyl ethyl vinyl ether,
1,3-dihydroxybutyl ethyl prop-1-enyl ether,
1,3-dihydroxybutyl octyl vinyl ether,
1,3-dihydroxyhexyl dodecyl but-1-enyl ether,
1,2-dihydroxybutenyl ethyl prop-1-enyl ether,
1,3-dihydroxyoctenyl ethyl vinyl ether,
1,3-dihydroxydecyl hexyl hex-1-enyl ether,
1,2-dihydroxyethyl phenyl vinyl ether,
1,3-dihydroxypropyl bromophenyl vinyl ether,
1,3-dihydroxyethyl chlorophenyl vinyl ether,
1,3-dihydroxyethyl tolyl vinyl ether,
1,3-dihydroxyethyl hydroxyphenyl vinyl ether,
1,3-dihydroxyethyl oxyphenyl vinyl ether,
1,3-dihydroxyethyl dibromohexyl vinyl ether,
1,3-dihydroxyethyl hydroxyoctyl vinyl ether,
1,2-dihydroxybutyl tolyl prop-1-enyl ether and the like.

Suitable examples of reactant II include dimethyl terephthalate, dimethyl-amino-terephthalate, dimethyl-amino-isophthalate, dimethyl adipate, dibutyl malonate, diethyl oxalate, dioctyl oxalate, didecyl malonate, diethyl succinate, dimethyl glutarate, dibutyl adipate, dioctyl succinate, didodecyl phthalate, etc.

The transesterification reaction of I and II is carried out in the liquid phase with agitation under a blanket of an inert gas. A temperature of between about 95° and about 210° C., preferably, between about 140° and about 180° C., for a period of from about 1 to about 5 hours. During reaction, the alcohol by-product is continuously removed by distillation; or, when the reaction is conducted in a sealed system, the by-product can be subsequently distilled off at above its vaporization temperature. The mole ratio of the polyhydroxy alk-1-enyl ether (I) to diester (II) is dependent on the number of functional —OH and R$_3$COO-groups in the respective reactants. Generally, a —OH to R$_3$COO— mole ratio of between about 1:1 and about 1:2.5 can be employed, however, a slight excess of reactant II is preferred. Further, this reaction can be carried out in the presence of from about 0.1 to about 3 wt. %, based on reaction mixture, of a catalyst such as titanium isopropoxide, titanium butoxide, titanium methoxide, sodium hydroxide, potassium hydroxide, sodium methoxide, sodium t-butoxide, potassium methoxide, potassium butoxide, sodium phenoxide, potassium phenoxide, zinc, zinc acetate, manganese acetate, dibutyl tin dioxide or another base catalyst.

The intermediate monomer or oligomer (III) is then reacted with an end capping compound, preferably a monohydroxy alk-1-enyl ether of the formula

HO-R$_4$-OCH=CHR$_6$ IV wherein R$_4$ is C$_1$ to C$_6$ alkylene, C$_6$ to C$_{14}$ arylene, xylylene, each optionally substituted with alkyl, halogen or alkenyl and R$_6$ is hydrogen or C$_1$ to C$_4$ alkyl. The resulting monomer or block oligomer of this invention having the formula

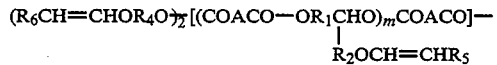

is obtained in quantitative yield.

The monohydroxy alk-1-enyl ether reactants (IV) include hydroxyhexyl prop-1-enyl ether, 1-hydroxydimethylene-propylene vinyl ether, hydroxyethyl-prop-1-enyl ether, hydroxycyclohexyl vinyl ether, hydroxybutylvinyl ether, hydroxybutyl but-1-enyl ether, hydroxypropyl prop-1-enyl ether, α-hydroxyoctyl-vinyl ether, 2-hydroxypropyl prop-1-enyl ether, hydroxyphenyl prop-1-enyl ether, hydroxy tolyl but-1-enyl ether, hydroxybutyl but-1-enyl ether, the vinyl ether or prop-1-enyl ether of hydroxymethyl benzyl alcohol, cyclohexane dimethanol mono vinyl ether, etc. The end capping reaction involving reactant IV is carried out under conditions similar to the reaction between reactants I and II including the presence of the base catalyst.

In the reaction between intermediate compound III and the end capping monohydroxy alk-1-enyl ether, a mole ratio of —COOR$_3$ to —OCH=CHR$_5$ between about 4:1 and about 1:4, preferably between about 1:1.5 and about 1:2 is employed. The Brookfield viscosity of the liquid prepolymeric product, which ranges from about 5,000 to about 500,000 cps, is inversely affected by the amount of end capping diluent added.

The above reactions can be effected in a single stage or in a two-stage process. In the single stage, the polyhydroxylated alk-1-enyl ether, the difunctional ester and the end capping component diluent are contacted with constant agitation under a pressure of from about atmospheric to about 20 psig.

The cationically curable prepolymer of this invention exhibits many advantages over the polyester prepolymers of the art in that the present prepolymer offers an increased number of crosslinking sites, which, when polymerized, provides a coating of extremely high density having excellent resistance to abrasion and chemical attack. The present prepolymer, obtained in a liquid state, allows for improved uniform coating applications on a substrate of metal, plastic, ceramic, wood, paper, glass, etc. The cured prepolymer also maintains flexibility resulting from their many unsaturated sites where polymer units are extended by addition to double bonds. Further, coatings of the present cured polymer preserve the finish of a painted surface, e.g. as automotive, aircraft and ship coatings. The present prepolymers III are prepared for curing by the addition of a cationic initiator and between about 10 and about 80 wt. % of a diluent.

The present prepolymers which are useful as high density curable molding resins and highly solvent resistant adhesive coatings. The product can be diluted with a suitable solvent, applied to a surface in a thickness of between about 0.1 to about 5 mils and cured by exposure to a source of radiation such as UV light, electron beam, laser emission, X-rays, gamma-rays, etc. in the presence of an onium photoinitiator such as, for example a diaryl iodonium salt, a polyphenyl sulphonium fluoride, a triaryl sulphonium salt and the like. Curing by UV light exposure is generally effected at between about 300 and about 3,000 milli joules/cm$^2$. Radiation curing of the prepolymer is extremely rapid, so that a coated substrate can be processed at a rate of up to 700 feet/sec and; whereas curing by heat requires a longer treatment up to about 2 hours. Examples of the reactive diluents employed in formulations of the present curable products are divinyl ether of triethylene glycol (DVE) and cyclohexane dimethanol divinyl ether (CHVE), the propenyl propylene ether of propylene carbonate (PEPC), tetrahydrofurfuryl vinyl ether and epoxides, e.g. 3,4-epoxycyclohexyl-3,4-epoxycyclohexane. The present coatings are clear, colorless, flexible films which find many applications as indicated above.

Having thus generally described the invention, reference is now had to the accompanying examples which illustrate comparative examples and preferred embodiments which are not construed as limiting to the scope of the invention as more broadly set forth above and in the appended claims.

EXAMPLE 1

Aromatic Polyester Resin (Prepolymer) Synthesis

Into a 500 cc round bottom flask, equipped with an agitator, temperature control, nitrogen sparge and a distillation head, was added 65.05 grams (0.50 moles) of 3-(1-propeneoxy)-1,2-propanediol; 194.19 grams (1.0 moles) or dimethyl terphthalate; 0.56 grams (0.0018 moles) of titanium (IV) isopropoxide; and 116.1 grams of 4-hydroxy butyl vinyl ether. The reaction was heated to 90° C. at which point methanol began to distill overhead. The reaction temperature was increased incrementally over a period of 16 hours to a temperature of 180° C. after which 95.0% of the stoichiometric methanol by-product was distilled overhead, and the reaction was terminated. The product,

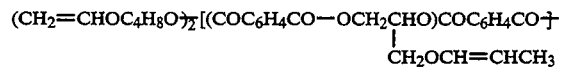

(305.2 grams) was recovered and its structure identified by H$^1$NMR and FTIR analysis. The product obtained in 97.9% yield was of high purity.

EXAMPLE 2

Aliphatic Polyester Resin (Prepolymer) Synthesis

Into a 500 cc round bottom flask, equipped with an agitator, temperature control, nitrogen sparge and a distillation head, was added 65.05 grams (0.50 moles) of 3-(1-propeneoxy)-1,2-propanediol; 174.19 grams (1.0 moles) or dimethyl adipate; 0.56 grams (0.0018 moles) of titanium (IV) isopropoxide; and 116.1 grams of 4-hydroxy butyl vinyl ether. The reaction was heated to 90° C. at which point methanol began to distill overhead. The reaction temperature was increased incrementally over a period of 16 hours to a temperature of 180° C. after which 95.0% of the stoichiometric methanol by-product was distilled overhead, and the reaction was terminated. The product, $$(CH_2=CHOC_4H_8O)_{\overline{x}}[(COC_4H_8CO-OCH_2CHO)COC_4H_8CO]-$$
$$\quad\quad\quad\quad\quad\quad\quad\quad\quad\quad\quad\quad\quad\quad\quad\quad\quad\quad |$$
$$\quad\quad\quad\quad\quad\quad\quad\quad\quad\quad\quad\quad\quad\quad\quad\quad\quad CH_2OCH=CHCH_3$$

(285.2 grams) was recovered and its structure identified by H1NMR and FTIR analysis. The product obtained in a yield of 97.9% was of high purity.

When

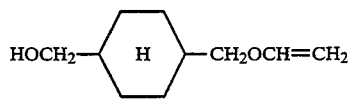

is substituted in the same molar amount in the above Example 2 for 4-hydroxybutyl vinyl ether, the product has the structure

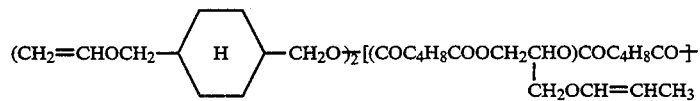

EXAMPLE 3

Halo-Aromatic Polyester Resin (Prepolymer) Synthesis

Into a 500 cc round bottom flask, equipped with agitation, temperature control, nitrogen sparge and a simple distillation head, was added 80.05 grams (0.50 moles) of 4-(1-buteneoxy)-1,2-butanediol; 262.2 grams (1.0 moles) of 2-(trifluoromethyl)-1,4-dimethyl terphthalate; 0.56 grams (0.0018 moles) of titanium (IV) isopropoxide; and 116.1 grams (1.0 moles) of 2-(1-buteneoxy)-1-ethanol. The reaction was heated to 90° C. after which methanol began to distill overhead. The reaction temperature was increased incrementally over a period of 16 hours to 180° C. At this point 95.0% of the stoichiometric methanol was distilled overhead, and the reaction was terminated. 385.9 grams product having the formula

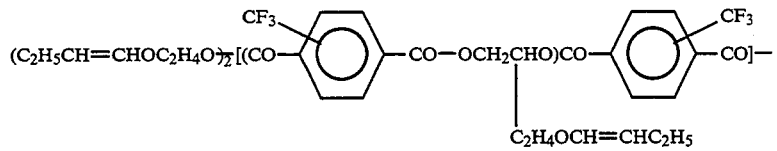

was recovered. H1NMR and FTIR analysis confirmed the structure and high purity of the product. An overall yield of 97.9% was obtained.

EXAMPLE 4

The products of Examples 1-3 were tested as radiation curable formulations containing 49% of the respective products, 49% of divinyl ether of triethylene glycol and 2% of triphenyl sulfonium salt initiator (FX-512). The resulting formulations were each coated on an aluminum panel and subjected to curing using a 400 mJ/cm2 PPG model QC-1202A/N U.V. processor. The coating performance of each of these formulations was compared and the results summarized in the following Table.

TABLE

| PRODUCT OF | PENCIL HARDNESS | ADHESION % | MANDRELL BEND | MEK RUBS | TENSILE PROPERTIES | | ELONGATION % |
| --- | --- | --- | --- | --- | --- | --- | --- |
| | | | | | YOUNGS MODULUS | TENSILE STRENGTH | |
| EXAMPLE 1 | H | 100 | 1/8 | >200 | 64 | 880 | 6.4 |
| EXAMPLE 2 | HB | 80 | 1/8 | >200 | 50 | 700 | 5.3 |
| EXAMPLE 3 | F | 70 | 1/8 | >200 | 50 | 650 | 5.1 |

Merely by increasing the mole ratio of the intermediate with respect to the end capping hydroxy alk-1-enyl ether in the above examples, a product where m has a value greater than 1 can be obtained. Accordingly, a 25-fold increase in the intermediate concentration produces a product where m is 25.

What is claimed is:

1. A polyalk-1-enyl polyester prepolymer having the formula

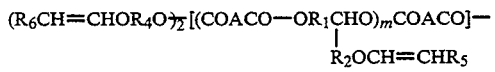
$$\quad\quad\quad\quad\quad\quad\quad\quad\quad\quad\quad\quad\quad |$$
$$\quad\quad\quad\quad\quad\quad\quad\quad\quad\quad\quad\quad R_2OCH=CHR_5$$

wherein m has a value of from 1 to 25;

A is $C_2$ to $C_{12}$ alkylene, $C_6$ to $C_{14}$ aryl, both groups optionally substituted with lower alkyl, halo lower alkyl, alkyleneoxy, halogen or aryl;

$R_1$ is alkylene containing from 1 to 6 carbon atoms;

$R_2$ is a saturated or unsaturated divalent radical containing from 1 to 14 carbon atoms and is selected from the group of alkylene, alkenylene and arylene, each group optionally substituted with oxygen, halogen, lower alkyl and/or hydroxy;

$R_3$ is hydrogen or $C_1$ to $C_6$ alkyl;

$R_4$ is $C_1$ to $C_6$ alkylene, $C_6$ to $C_{14}$ arylene, lower alkyl substituted phenylene or xylylene $R_5$ is hydrogen or $C_1$ to $C_4$ alkyl, $R_6$ is hydrogen or $C_1$ to $C_4$ alkyl.

2. The prepolymer of claim 1 wherein A is aryl and m has a value of 2.

3. The prepolymer of claim 1 wherein A is an aliphatic radical and m has a value of 2.

4. The prepolymer of claim 1 having the formula:

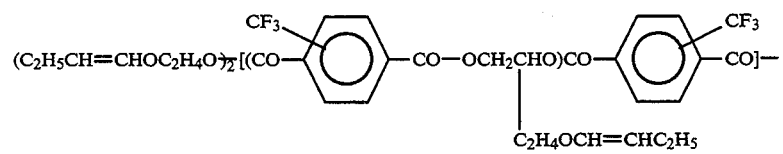

5. The prepolymer of claim 1 having the formula:

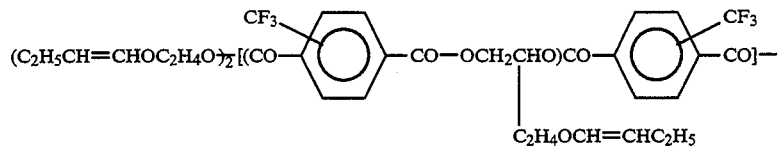

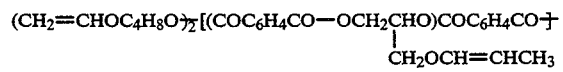

6. The prepolymer of claim 1 having the formula:

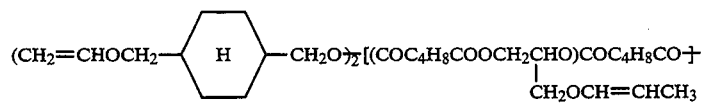

7. The prepolymer of claim 1 having the formula:

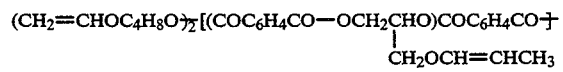

8. A radiation curable composition containing the prepolymer of claim 1 and an effective amount of a cationic polymerization initiator.

9. The composition of claim 8 wherein said initiator is an onium salt initiator.

10. The composition of claim 9 wherein said initiator is the triphenylsulfonium salt of hexafluorophosphate.

11. The composition of claim 9 wherein said prepolymer has the formula:

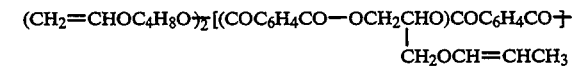

12. The composition of claim 9 wherein said prepolymer has the formula:

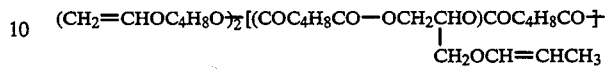

13. The composition of claim 9 wherein said prepolymer has the formula:

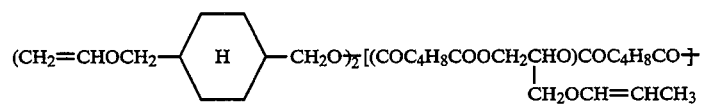

14. The composition of claim 9 wherein said prepolymer has the formula:

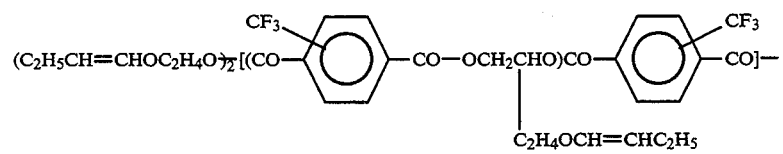

15. A substrate having a hard, durable and flexible coating of the cured prepolymer of claim 1.

16. The substrate of claim 15 which is coated with the cured prepolymer having the formula:

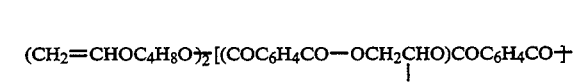

17. The substrate of claim 15 which is coated with the cured prepolymer having the formula:

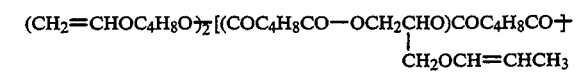

18. The substrate of claim 15 which is coated with the cured prepolymer having the formula:

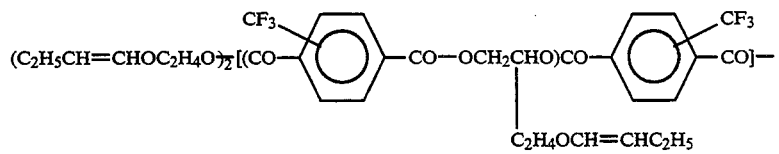
19. The substrate of claim 15 which is coated with the cured prepolymer having the formula:
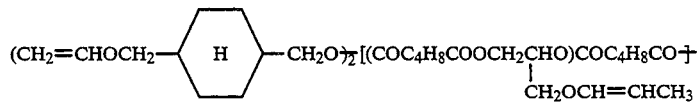
* * * * *